United States Patent [19]
Nöldner et al.

[11] Patent Number: 6,022,889
[45] Date of Patent: Feb. 8, 2000

[54] PHARMACEUTICAL PREPARATIONS CONTAINING BILOBALIDE FOR THE TREATMENT OF TENSION AND ANXIETY

[75] Inventors: Michael Nöldner, Eggenstein; Shyam S. Chatterjee, Karlsruhe, both of Germany

[73] Assignee: William Schwabe GmbH & Co., Karlsruhe, Germany

[21] Appl. No.: 08/244,900

[22] PCT Filed: Dec. 22, 1992

[86] PCT No.: PCT/EP92/02981

§ 371 Date: Jul. 14, 1994

§ 102(e) Date: Jul. 14, 1994

[87] PCT Pub. No.: WO93/12784

PCT Pub. Date: Jul. 8, 1993

[30] Foreign Application Priority Data

Dec. 23, 1991 [DE] Germany .............................. 41 42 878

[51] Int. Cl.[7] .................................................... A61K 31/34
[52] U.S. Cl. ............................................................ 514/468
[58] Field of Search ............................................... 514/468

[56] References Cited

U.S. PATENT DOCUMENTS 4,571,407  2/1986  Chatterjee et al. ..................... 514/464

FOREIGN PATENT DOCUMENTS 0143977  12/1986  European Pat. Off. .
2023421  1/1980  United Kingdom .

OTHER PUBLICATIONS

Investigatión Medica Internacional, vol. 17, No. 3 (1990), pp. 130–141.
La Presse Médicale, vol. 15, No. 31, Sep. 25, (1986), pp. 1595 to 1604.
Fortschritte der Medizin, vol. 108, No. 29, Oct. 10, (1990), pp. 557–560.
Chem. Abstracts, Oct. 22, (1990), vol. 113, No. 17, p. 664, CA 113:151138d.

*Primary Examiner*—Kimberly Jordan
*Attorney, Agent, or Firm*—Birch, Stewart, Kolasch & Birch. LLP

[57] ABSTRACT

The invention suggests a novel medical use of pure bilobalide or Ginkgo biloba extract with an increased bilobalide content as an anxiolytic or antidepressant.

8 Claims, 9 Drawing Sheets

Table A — Elevated Plus Maze
Substance administered 60 mins. prior to testing
Means ± sd from n = 8 Sprague Dawley rats, male
Time of observation = 5 mins.

| Substance | Dose mg/kg | Time rats stayed in open arm (sec.) M | sd | Time rats stayed in closed arm (sec.) M | sd | Entries into open arm n M | sd | Entries into closed arm n M | sd | Open arm % of total | Remarks |
|---|---|---|---|---|---|---|---|---|---|---|---|
| Control | 10ml/kg p.o. | 60.0 | 7.1 | 201.5 | 20.4 | 7.3 | 1.4 | 8.3 | 2.4 | 48% | |
| Diazepam | 0.1 p.o. | 72.9* | 7.1 | 201.8 | 11.0 | 6.8 | 1.4 | 7.0 | 2.1 | 49% | |
| Diazepam | 0.5 p.o. | 85.9** | 9.5 | 176.1* | 19.6 | 8.8 | 2.6 | 8.4 | 2.6 | 51% | |
| Diazepam | 2.5 p.o. | 110.4** | 13.2 | 158.8** | 18.6 | 9.6* | 2.6 | 8.5 | 3.1 | 53% | |
| Control | 10ml/kg p.o. | 49.5 | 5.7 | 219.4 | 10.8 | 7.1 | 2.7 | 8.4 | 3.0 | 46% | |
| Bilobalide | 1 p.o. | 63.7** | 6.3 | 193.1* | 19.1 | 8.3 | 1.8 | 8.5 | 2.2 | 49% | |
| Bilobalide | 5 p.o. | 74.6** | 6.6 | 186.1** | 15.8 | 9.9* | 2.4 | 10.3 | 2.8 | 49% | |
| Bilobalide | 20 p.o. | 87.6** | 6.6 | 189.0** | 8.6 | 6.8 | 1.9 | 7.1 | 3.6 | 49% | |
| Control | 10ml/kg p.o. | 54.4 | 13.3 | 209.6 | 20.6 | 7.4 | 1.6 | 9.4 | 1.2 | 44% | |
| Ethanol | 0.5g/ p.o. | 60.7 | 2.5 | 206.1 | 8.3 | 7.8 | 0.7 | 10.0 | 1.9 | 44% | |
| Ethanol | 1 g/ p.o. | 83.3** | 6.4 | 190.8* | 9.1 | 10.6* | 2.3 | 9.5 | 2.7 | 50% | |
| Ethanol | 2 g/ p.o. | 98.9** | 7.5 | 170.9* | 18.8 | 12.9** | 2.5 | 11.9* | 2.7 | 52% | |
| Control days 1–5 | 10ml/kg p.o. | 59.0 | 11.0 | 187.0 | 17.3 | 8.3 | 1.9 | 11.1 | 1.9 | 43% | Treatment: Days 1–4 agar Day 5 agar |
| Bilobalide day 5 | 5 p.o. | 81.5** | 5.9 | 187.9 | 13.3 | 11.6* | 2.0 | 9.0 | 2.7 | 56% | Days 1–4 agar Day 5 bilob. |
| Bilobalide days 1–5 | 5 p.o. | 91.2** | 9.8 | 176.3 | 18.3 | 10.6* | 1.4 | 7.9* | 1.3 | 57% | Days 1–5 bilob. |

\* ≤ 0.05   \*\* ≤ 0.001   Student's t-test using controls in each case

FIG. 1

Light/Dark Box
Substance administered 60 mins prior to testing        Time of observation = 3 minutes
Means ± s.d. from n = 10 NMRI mice, male

| Substance | Dose (mg/kg) | Light field (sec.) M ± s.d. | | Switches (n) M ± s.d. | |
|---|---|---|---|---|---|
| Control | 10 ml/kg p.o. | 75.3 | 7.7 | 13.2 | 3.4 |
| Diazepam | 0.1 p.o. | 94.8 * | 13.6 | 14.8 | 5.1 |
| Diazepam | 0.5 p.o. | 113.5 ** | 12.8 | 11.6 | 2.1 |
| Diazepam | 2.5 p.o. | 115.8 ** | 14.9 | 11.2 | 4.1 |
| Diazepam | 12.5 p.o. | 153.3 ** | 22.1 | 4.8 * | 6.9 |
| Control | 10 ml/kg i.p. | 75.8 | 9.2 | 12.5 | 2.8 |
| Buspiron | 2.5 i.p. | 80.9 | 11.5 | 11.8 | 3.7 |
| Buspiron | 5 i.p. | 78.0 | 9.7 | 12.1 | 2.2 |
| Buspiron | 10 i.p. | 112.0 ** | 15.1 | 16.1 * | 3.3 |
| Control | 10 ml/kg p.o. | 76.8 | 11.8 | 9.8 | 2.6 |
| Bilobalide | 5 p.o. | 78.6 | 7.8 | 10.4 | 2.4 |
| Bilobalide | 10 p.o. | 86.3 | 17.1 | 8.4 | 1.4 |
| Bilobalide | 20 p.o. | 106.2 * | 34.6 | 7.2 | 3.2 |

\* p ≤ 0.05    Student's t-test using controls in each case
\*\* p ≤ 0.001

Control    Bilobalide
Student's t-test using controls in each case

★ p ≤ 0.05
★★ p ≤ 0.001

Student's t-test using controls in each case

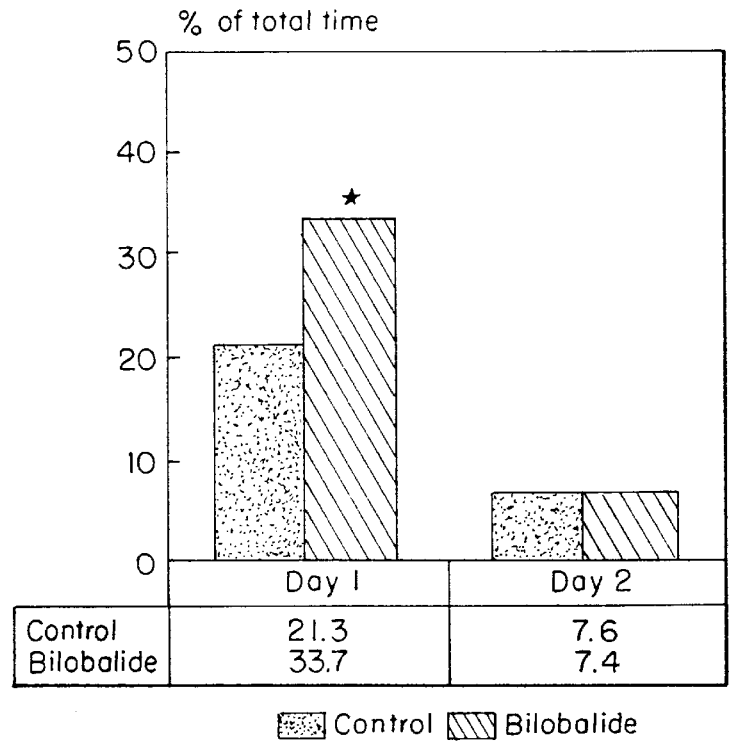
FIG. 4C Bilobalide — Time spent in the open side arms
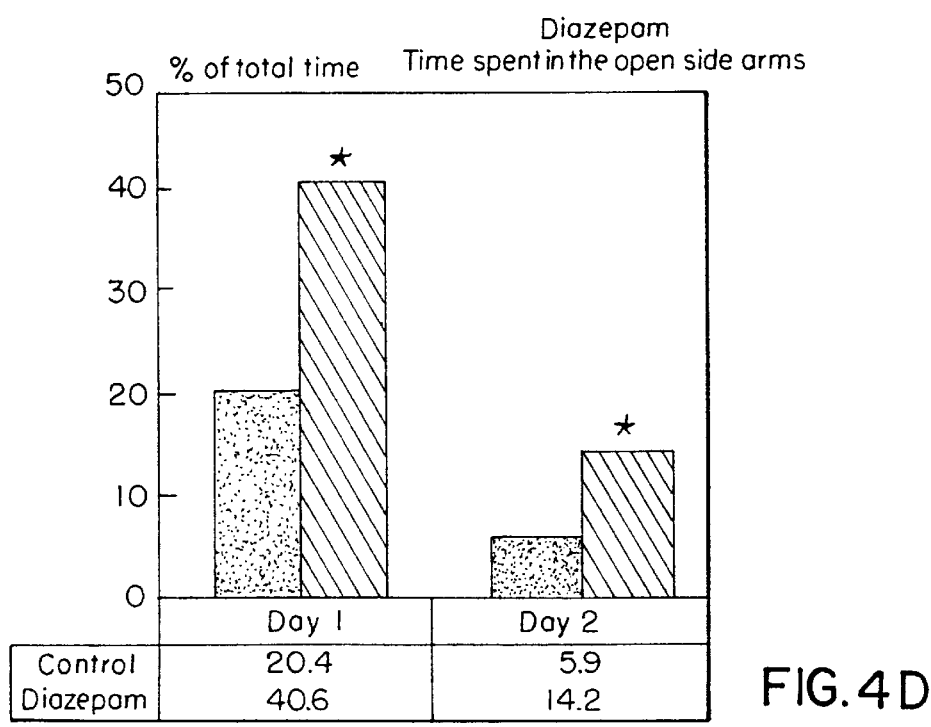
FIG. 4D Diazepam — Time spent in the open side arms
★ p ≤ 0.05
★★ p ≤ 0.001
Student's t-test using controls in each case ★ p≤0.05
★★ p≤0.001

Student's t-test using controls in each case

PHARMACEUTICAL PREPARATIONS CONTAINING BILOBALIDE FOR THE TREATMENT OF TENSION AND ANXIETY

This application is a 371 of PCT/EP92/02981, filed Dec. 22, 1992.

BACKGROUND OF INVENTION

R. T. Major (Science 157, 1967, 1270–1273) was the first person to report on the isolation of a lactone having the formula $C_{15}H_{18}O_8$ from the leaves of the Ginkgo biloba tree. K. Weinges and W. Bähr termed the substance "bilobalide" and investigated and described the physicochemical properties of bilobalide and its derivatives (Liebigs Ann. Chem., 724, 1969, 214–216). According to a joint publication by the research teams of K. Nakanishi et al., R. T. Major et al., and K. Weinges et al. (J. Amer. Chem. Soc. 93, 1971, 3544–3546), bilobalide has the formula I

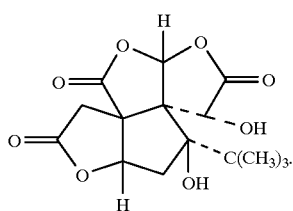

Since 1965 extracts from leaves of the Ginkgo biloba tree have been used in the therapy of central and peripheral circulatory disturbances. Such extracts contain flavone glyocsides as their main components and have also been standardized to include those ingredients. A typical representative of this group is 5,7,3',4'-tetrahydroxyflavono-3-O-alpha-rhamnopyranosyl-4-O-beta-D-(6'''-trans-cumaroyl) glycopyranoside having the formula II Generally, those extracts may also contain lower amounts of bilobalide and ginkgolides A, B, C, and J.

U.S. Pat. No. 4,571,407 discloses that bilobalide is useful in the treatment of various degenerative, neuronal diseases. Such diseases particularly include neuropathies, encephalopathies, and myelopathies associated with one or more of the following symptoms: paresthesias, pareses, abnormal reflexes, muscular atrophies, muscular spasms, tremors, headaches, speech disorders, hearing defects, dizziness, disturbances of consciousness, impaired coordination, etc.

Surprisingly, it has now been found that bilobalide exhibits anxiolytic activities in addition to the known pharmacological effects on degenerative, neurological diseases. This is the first time that psychopharmacological effects of bilobalide have become known.

The fear that actually represents a useful mechanism to protect the human being in that it frequently warns him against exposing himself to certain dangers becomes pathological when it is unfounded or extremely strong. Anxiety patients show, among others, symptoms such as agitation, unrest, apathy and frequently have difficulty in falling asleep and in sleeping through.

Pathological fear is a frequently occurring symptom that is often not paid enough attention to, although fear is frequently the cause of so-called psychosomatic diseases. Pathological fear has so far been treated by psychotherapy and/or drug therapy using anxiolytic drugs.

The pharmacological anxiolytics are predominantly derived from the group of benzodiazepines (e.g., diazepam). More recent anxiolytics have been characterized pharmacologically as $5HT_{1a}$ agonists (e.g., buspiron). Surprisingly, bilobalide shows activity essentially corresponding to that of diazepam or buspiron in various animal models.

SUMMARY OF INVENTION

Thus the invention relates to the use of bilobalide or Ginkgo biloba extracts supplemented with bilobalide as an anxiolytic. In preferred embodiments it is used for the treatment or prophylaxis of anxiety, tension and depressive conditions.

BRIEF DESCRIPTION OF DRAWINGS

FIG. 1 shows Table A which summarizes the administered substances, dosages, and observations of rats subjected to elevated plus maze tests.

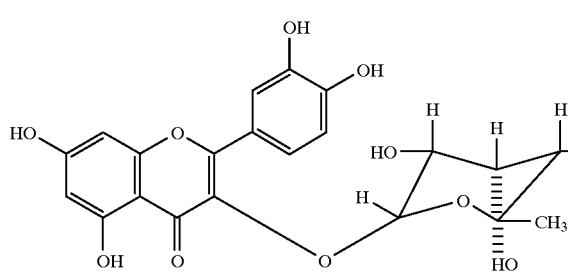
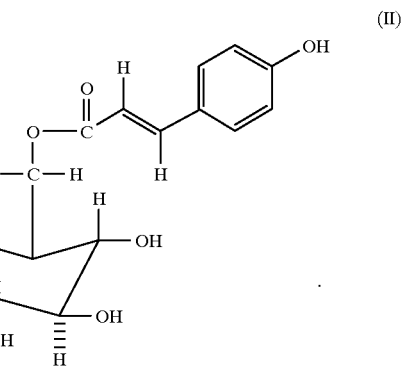

FIG. 2 shows Table B which summarizes the administered substances, dosages and observations of mice subjected to light/dark box tests.

FIGS. 3a–3d are graphs showing the influence of bilobalide, diazepam and ethanol on the time that the rats spent in the open arm of the elevated plus maze.

FIGS. 4a–4d are graphs showing the influence of bilobalide and diazepam on the frequency with which the rats switched side arms and on the time they stayed on the open side arms in the elevated plus maze tests.

Figure 3A:
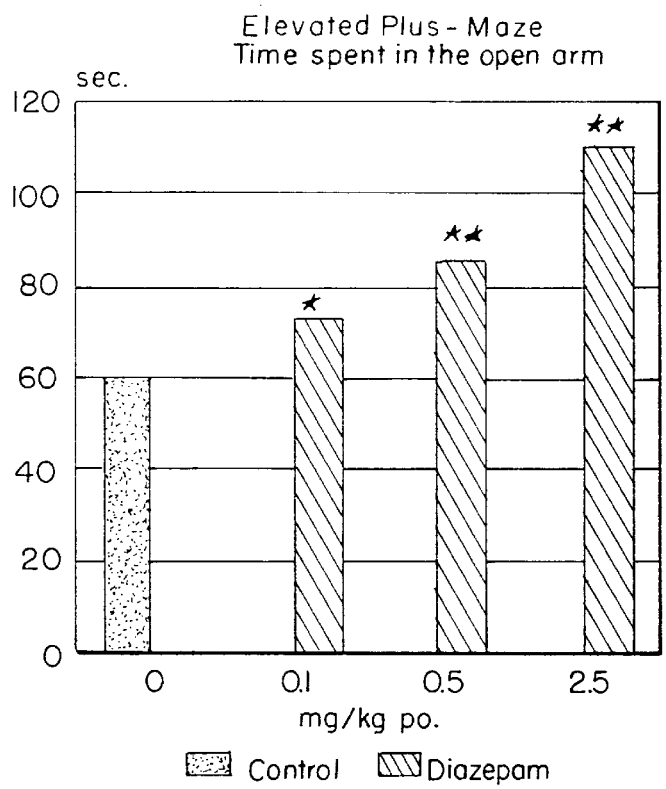
Figure 3B:
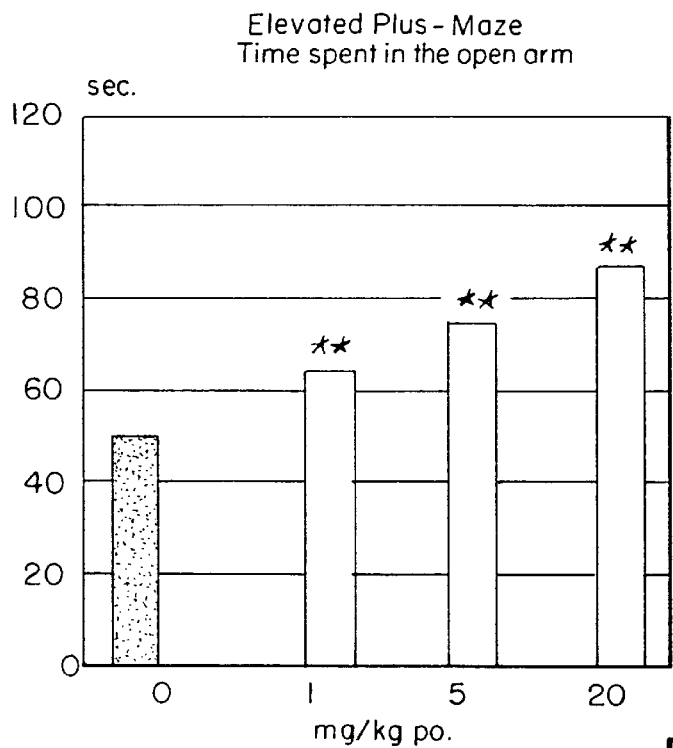
Figure 3C:
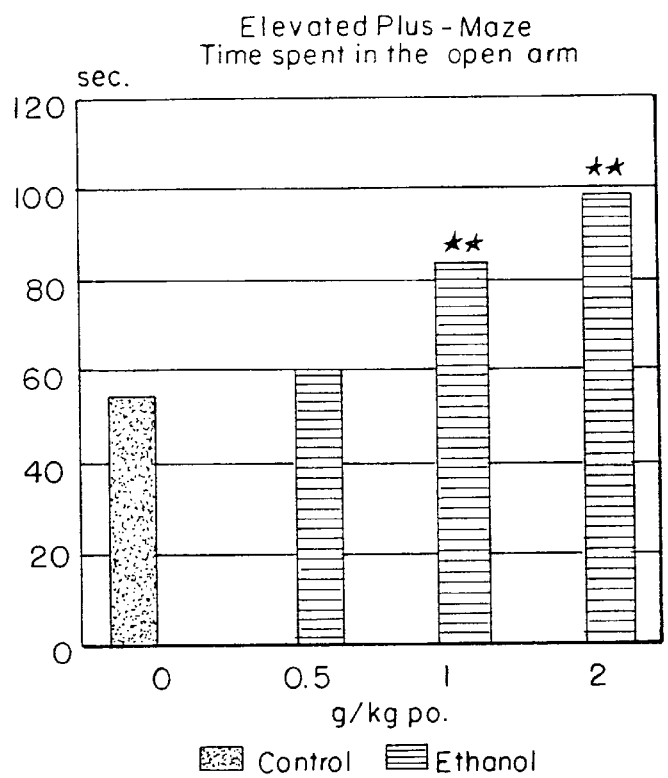
Figure 3D:
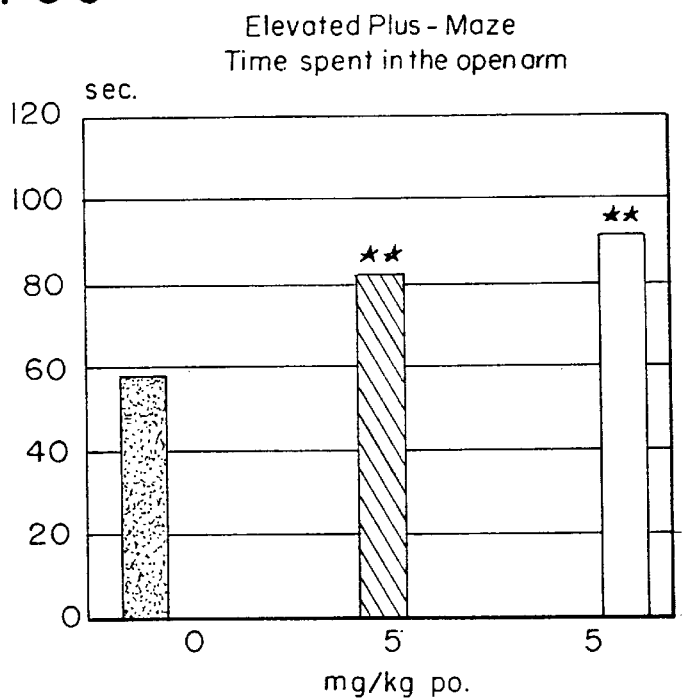
Figure 4A:
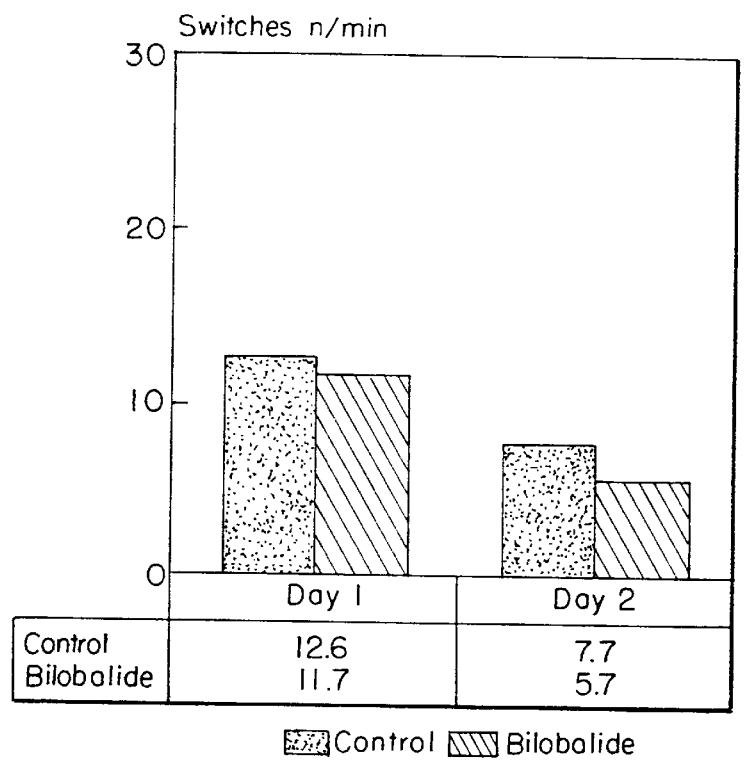
Figure 4B:
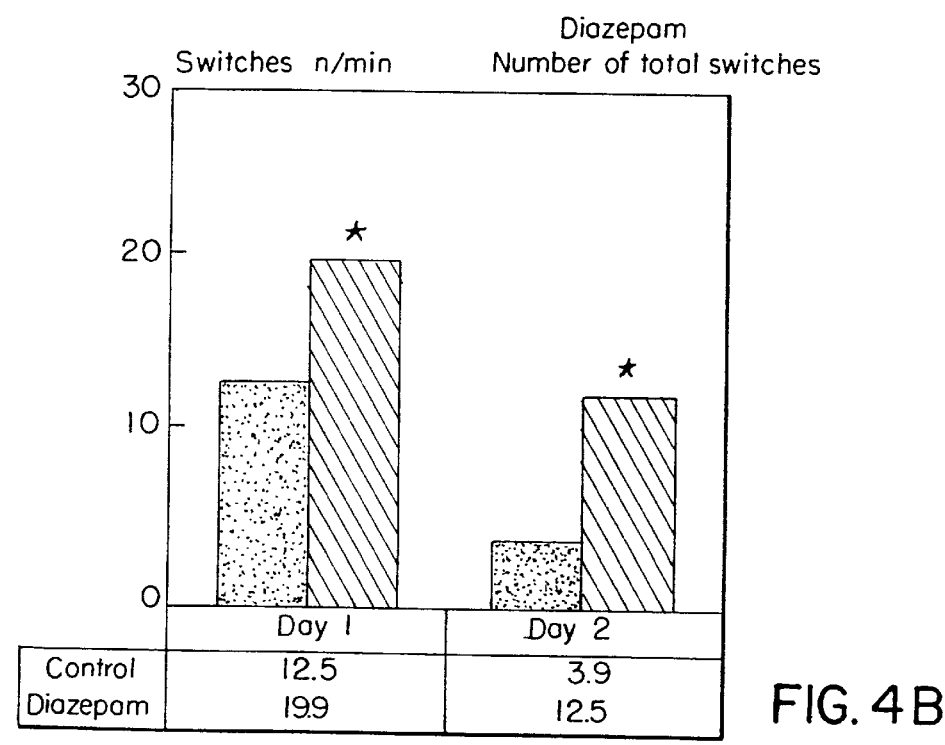
Figure 5A:
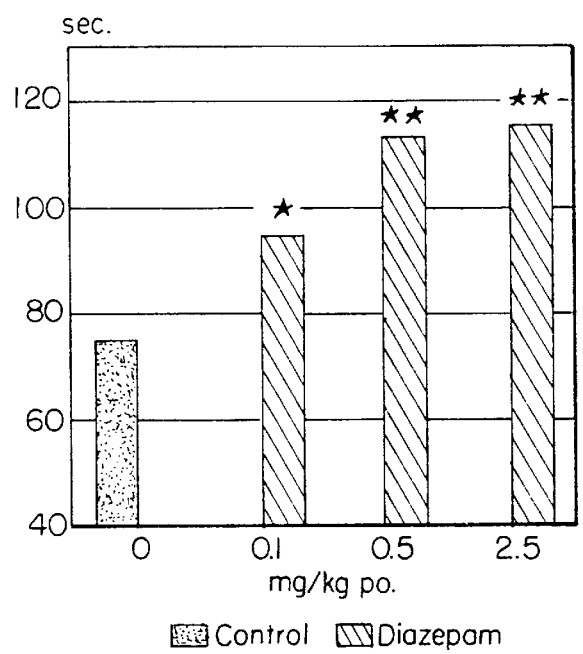
Figure 5B:
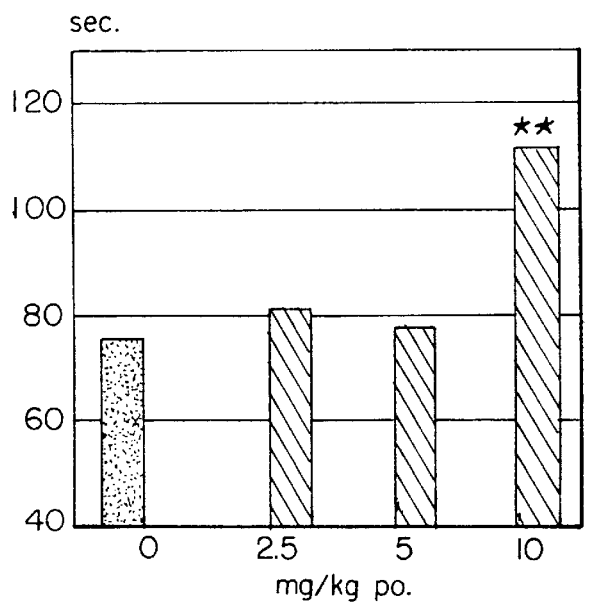
Figure 5C:
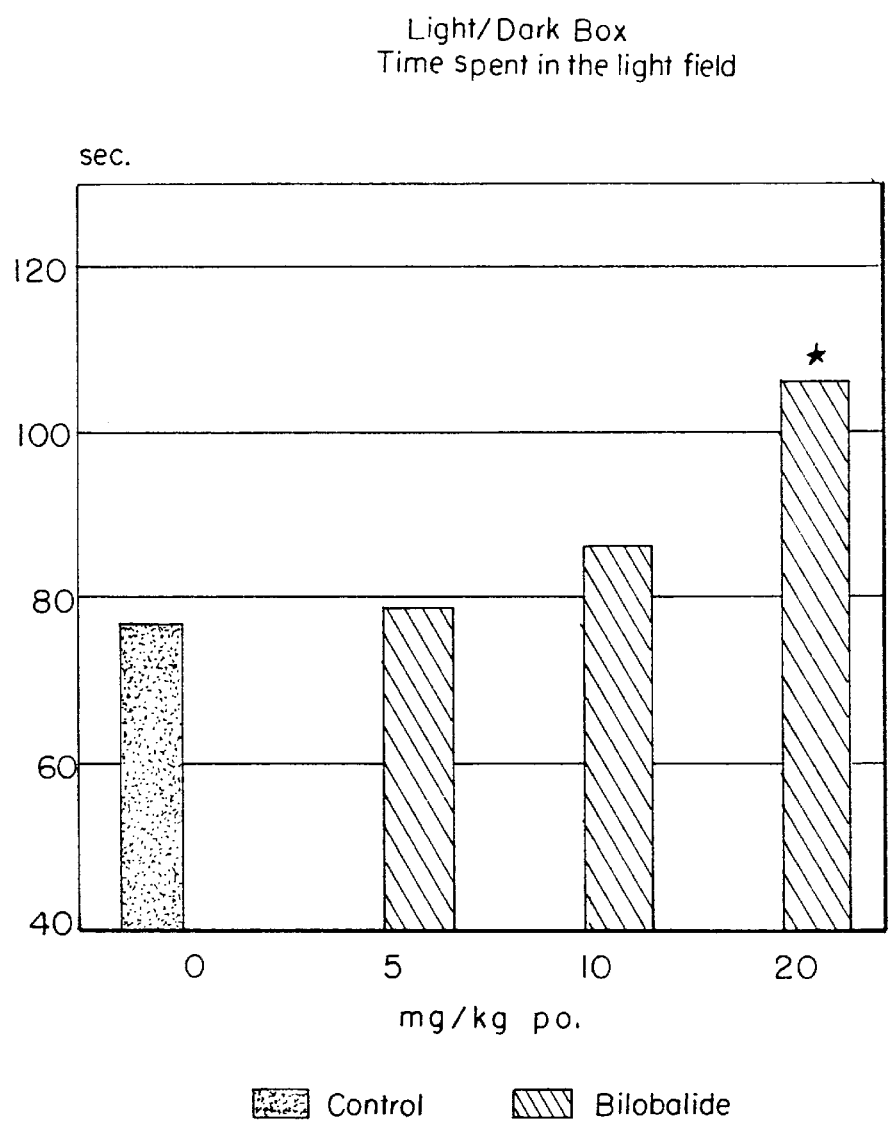

FIGS. 5a–5c are graphs showing the influence of bilobalide and diazepam and buspiron on the time that mice spent in the light compartment of the light/dark box.

Figure 6:
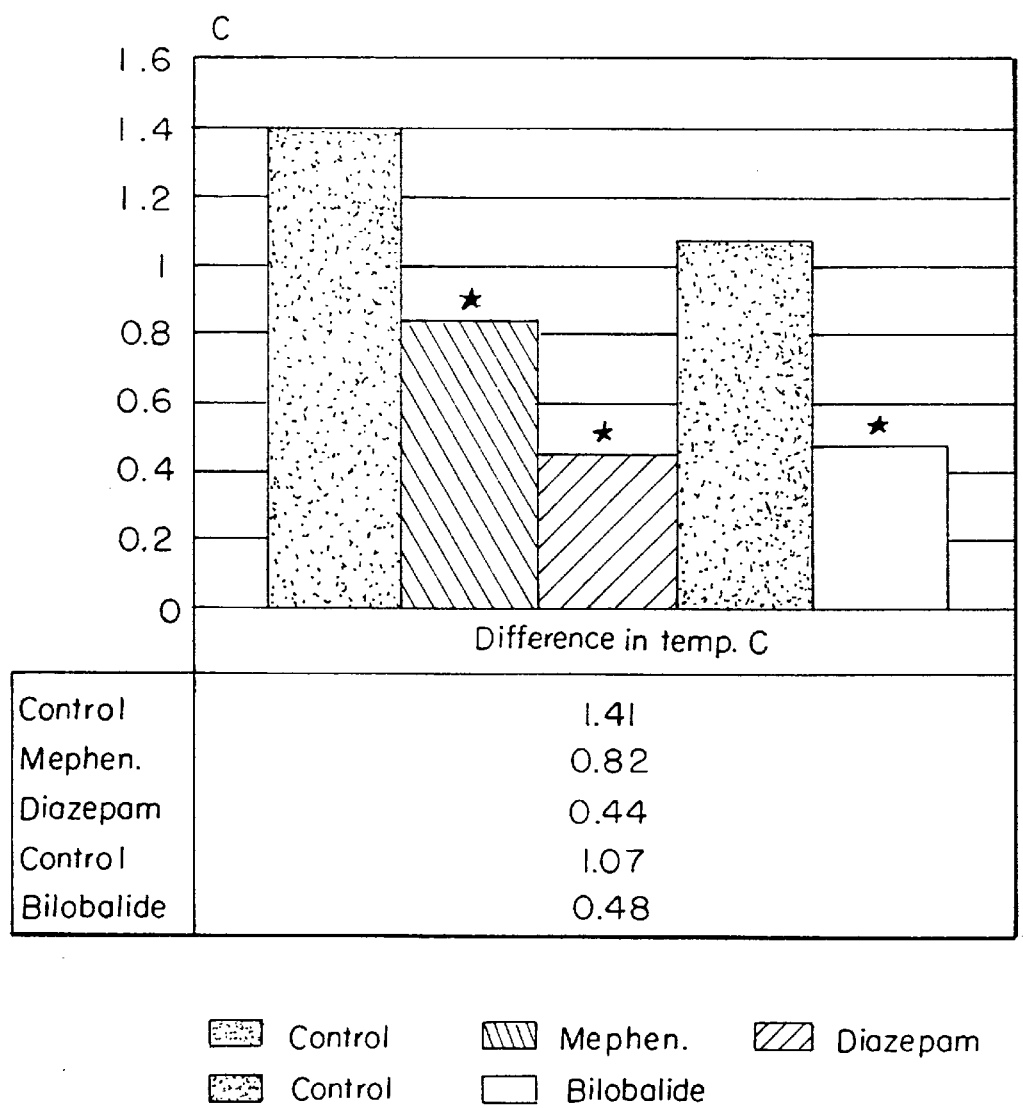

FIG. 6 is a graph showing the influence of bilobalide, diazepam and mephenesin on a stress-induced increase in temperature.

DETAILED DESCRIPTION OF INVENTION

The animal models used for the detection of anxiolytic activity were (1) the elevated plus maze, (2) the light/dark box, and (3) the fear-induced increase in temperature.

1. In the elevated plus maze test rats were placed in the center of the maze, and their behavior was studied for 5 minutes. Control animals showed normal exploratory behavior but stayed in the "secure" region of the dark side arms of the maze for most of the time. Anxiolytic drugs prolonged the time the test animals stayed in the maze and increased the frequency with which they switched to the "insecure" open side arms of the maze. (Lister, R. G. [1990], Ethologically-based animal models of anxiety disorders; Pharmac. Ther., 46, 321–340).

2. In the light/dark box experiment mice or rats were placed in the light field, and their behavior was observed for 3 minutes. Control animals showed a preference for the light/dark box in addition to normal exploratory behavior. Anxiolytics modified the animals' behavior such that the time they stayed in the light field was prolonged (Lister, R. G. [1990], Ethologically-based animal models of anxiety disorders; Pharmac. Ther., 46, 321–340).

3. In the model of the fear-induced increase in temperature mice were gathered in groups of 18 animals per cage and removed from the cage one after the other, held for about 20 seconds and were put back in the same cage. The body temperature of the first three and last three mice was taken rectally. On average, the temperature of the last mice was 1–1.5° C. higher than that of the first three animals. Such induced increase in temperature could be inhibited by anxiolytic drugs effective in humans. (Lecci, A. et al. [1990], Pharmacological validation of a novel animal model of anticipatory anxiety in mice; Psychopharmacology, 101, 225–261).

The effectiveness of bilobalide has been demonstrated by the following experiments:

Experiment 1a: Elevated Plus Maze

Male Sprague Dawley rats with a weight of 150–250 g were once administered perorally bilobalide in doses of 5, 10, or 20 mg/kg in 10 ml of 0.2% agar suspension 60 minutes prior to testing. Control animals were administered perorally agar only, reference animals were given diazepam or ethanol. A highly significant effect was apparent both after administration of a single dose and after repeated bilobalide administration (once daily for 5 days).

Experiment 1b: Elevated Plus Maze

In a test setup constituting a modification of the above model rats were not placed in the center of the maze at the beginning of the experiment. Instead, they were put at the outermost end of an open side arm, with their faces directed outwardly. The test was conducted for two consecutive days using the same animals. On day 2 of the experiment, the rats stayed in the open arms for a substantially shorter time and, accordingly, switched maze arms with reduced frequency. This was a phenomenon that could be interpreted as learning because the rats knew the maze by day 2 of the experiment and quickly reached their destination.

It has been possible to show by way of this test setup that the standard substance diazepam prolongs the time the animals stay in the open arm, which can be interpreted as anxiolytic activity, although the rats, despite being trained, switch side arms as frequently as untrained control rats.

In the case of bilobalide treated rats, too, the time the animals stay in the open arm is prolonged and the frequency with which they switch maze arms is reduced. This result indicates that bilobalide, unlike diazepam, does not affect the learning behavior of the animals despite its anxiolytic activity.

The results of the above experiments are shown in Table A of FIG. 1 and FIGS. 3A–3D and 4A–4D. More specifically, FIGS. 3A–3D show the influence of bilobalide, diazepam and ethanol on the time the rats spent in the open arm of the elevated plus maze; and FIGS. 4A–4D show the influence of bilobalide and diazepam on the frequency with which the rats switched side arms and the time they stayed in the open side arms.

Experiment 2: Light/Dark Box

In this experiment male NMRI mice with a weight of 20–30 g were administered perorally using a probang bilobalide in doses of 1, 5 and 20 mg/kg once daily 60 minutes prior to testing. Control animals were given (0.2%) agar suspension, reference animals diazepam, buspiron, or ethanol. In this model bilobalide, like the reference substances diazepam, buspiron and ethanol, showed clear, statistically significant effects equivalent to anxiolytic activity.

The results of the above studies are shown in Table B of FIG. 2 and FIGS. 5A–5C. More specifically FIGS. 5A–5C show the influence of bilobalide, diazepam, and buspiron on the time the mice spent in the light compartment of the light/dark box.

Experiment 3: Temperature Test

In this model bilobalide, when administered perorally in a dosage of 20 mg/kg, showed a clear, statistically significant reduction of the stress-related increase in temperature. The activity of bilobalide is comparable to that of the reference substances diazepam and mephenesin.

The results are shown in FIG. 6. More specifically, FIG. 6 shows the influence of bilobalide, diazepam, and mephenesin on the stress-induced increase in temperature.

In all test models selected herein bilobalide exhibits pharmacological effects indicating anxiolytic activity.

Bilobalide can be administered orally or parenterally, e.g., intramuscularly or intravenously, in the form of conventional drugs, e.g., solutions, coated tablets, tablets, capsules, injection or infusion solutions. The dosage depends on the gravity of the disease and the weight of the patient. Coated tablets can be given in the morning and in the evening following food intake. Daily doses range from 5 to 40 mg of bilobalide for usual formulations and 0.5 to 5 mg of bilobalide for parenteral application.

Bilobalide can be isolated, for example, from Ginkgo biloba leaves by the method reported by K. Weinges and W. Bähr, Justus Liebigs Ann. Chem., 724 (1969), 214–216.

Conventional carriers and additives can be used in the production of pharmaceutical compositions containing bilobalide. Examples of conventional carriers include water, physiological saline solution, alcohols, polyethylene glycols, glycerol esters, gelatin, carbon hydrates such as lactose and starch, magnesium stearate, talcum. Examples of conventional additives include preservatives, sterilizing agents, lubricants, wetting agents, emulsifiers, pigments, masking flavors, and aromatics. The selection of the carriers and additives depends on whether the preparations of the invention are to be administered enterally or parenterally.

1. Tablets containing pure bilobalide

The following ingredients are required to prepare tablets of 100 mg containing 5 mg of bilobalide each:

| | |
|---|---|
| 5 g | bilobalide |
| 58.5 g | lactose |
| 18 g | microcrystalline cellulose |
| 18 g | corn starch |
| 0.5 g | magnesium stearate |

The first four components are mixed, granulated and, after the addition of magnesium stearate, they are compressed to tablets in a tabletting machine.

2. Tablets containing bilobalide-containing Ginkgo extract

When Ginkgo extract supplemented with bilobalide is used, the following ingredients are required:

| | |
|---|---|
| n g | Ginkgo extract corresponding to 5 mg bilobalide |
| (200-n) g | lactose |
| 25 g | microcrystalline cellulose |
| 24 g | corn starch |
| 1 g | magnesium stearate |

The first four components are mixed, granulated and, after the addition of magnesium stearate, they are compressed to tablets of 250 mg each in a tabletting machine.

3. Capsules

| | |
|---|---|
| 7 g | bilobalide |
| 75 g | lactose |
| 20 g | corn starch |

The components are homogeneously mixed and processed in a conventional manner to capsules having a net weight of 100 mg.

4. Injection vials

The following ingredients are required to prepare 2 ml injection vials containing 0.5 mg of bilobalide:

| | |
|---|---|
| 0.25 g | bilobalide |
| 9 g | sodium chloride |
| ad 100 g | double destilled water |

The first two components are dissolved in water by slightly heating and stirring. The solution is filtrated under sterile conditions and filled in 2 ml vials.

5. Liquid oral formulations

| | |
|---|---|
| 5 g | bilobalide |
| 10 g | aroma essence |
| 5 g | sodium saccharinate |
| 400 g | ethyl alcohol |
| 580 g | destilled or deionized water |

The first three components are dissolved in a mixture of ethanol and water. The resulting solution is filled in 100 ml flasks. A single dose is 1 ml.

We claim:

1. A method for the treatment or prophylaxis of anxiety and tension comprising administering an effective amount of an active ingredient of bilobalide or Ginkgo biloba extract supplemented with bilobalide to patients in need of such treatment or prophylaxis.

2. The method of claim 1, wherein the bilobalide is substantially pure.

3. The method of claim 1, wherein said active ingredient is bilobalide.

4. The method of claim 1, wherein the bilobalide is administered in a dosage range of from 0.5 to 40 mg.

5. A method for the treatment or prophylaxis of depressive conditions comprising administering an effective amount of an active ingredient of bilobalide or Ginkgo biloba extract supplemented with bilobalide to patients in need of such treatment or prophylaxis.

6. The method of claim 5, wherein the bilobalide is substantially pure.

7. The method of claim 5, wherein said active ingredient is bilobalide.

8. The method of claim 5, wherein the bilobalide is administered in a dosage range of from 0.5 to 40 mg.

* * * * *